May 16, 1972 D. STURROCK Plant Pat. 3,181

NEW AND DISTINCT VARIETY OF MANGO

Filed Dec. 18, 1969

FIG. 1

FIG. 3

FIG. 2

David Sturrock

By: Hall M. McCaig attorney

United States Patent Office

Plant Pat. 3,181
Patented May 16, 1972

3,181

DISTINCT VARIETY OF MANGO

David Sturrock, 1020 Camellia Road,
West Palm Beach, Fla. 33480

Filed Dec. 18, 1969, Ser. No. 886,431
Int. Cl. A01h *5/03*
U.S. Cl. Plt.—33 1 Claim My new variety of mango, *Mangifera indica* L., is a result of my planned breeding efforts carried on personally in 1956 and selectively eliminating undesirable progeny and vegetatively propagating the desirable progeny. This variety is a result of crossing the monoembryonic hybrid Edward with the monoembryonic hybrid Kent.

The geneology of this new variety of mango is:

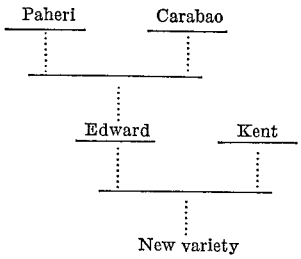

In the following season of 1956, branchlets with flower panicles of the Edward variety were marked and mingled with branchlets of the Kent variety having flower panicles. Upon maturity of the Edward fruits, the seeds of Edward were extracted, hulled and planted. The seedlings, thus obtained, were inspected regularly and those showing susceptibility to scab or anthracnose were discarded, by 1958 there remained 20 seedlings of the original progeny. To hasten growth maturity for fruiting, these seedlings were fastened and inarched to branches of older mango trees, the joinder being strenghtened with rubber bands overlaid with horticultural tape. In 1963 five of those vegetatively propagated varieties fruited; four were discarded as undesirable, and the other vegetatively extended. In 1964 and 1965 the remainder of these seedlings fruited and were discarded as undesirable; only one remained and, after further testing for a period of three years, was named the "Young" variety in honor of Dr. T. W. Young, of Vero Beach, Fla.

The principal distinguishing feature of the variety is the fruit, as illustrated in FIG. 1, showing the color of the fruit; FIG. 2 showing the color of the fruit, the flesh, lack of fiber; and FIG. 3 showing the comparative size of the seed, and the lack of fiber when taken in conjunction with FIG. 2. Color chart designations are according to Maerz and Paul's Dictionary of Color (1950 edition.)

*Fruit*

The variety generally bears one fruit, occasionally two, on stems medium in length, the fruits being quite uniform in size, shape and color.

The fruit is round-oval in shape, with a high ventral shoulder, the stem being inserted in a slight depression. The thick, smooth skin of the ripe fruit is golden-yellow (9–L4) in color, with a faint pink blush on the exposed side. The entire fruit is thickly spotted with pale yellow (9–J1) dots when ripe. The fiberless flesh is pale yellow, with a slightly darker band (9–L2) adjacent to the skin, of a fine texture and mild, sweet flavor. The seed hull is quite flat with slight fibers on the dorsal edge. The small seed is monoembryonic. The weight of the fruit is 18–22 oz., the length is 4½–5 inches, the width is 4–4¼ inches, the thickness is 3½ inches, as illustrated in FIG. 2. The season of fruit maturity is July and early August, annually.

*Leaf*

The leaf is simple, lanceolate, coriaceous. The blade, without petiole, is 7–8 inches long and 2–2½ inches wide. It is dark green and glossy on the upper surface and has fine, light green veins. The older blades are slightly twisted, tapering to a long sharp tip. The base of the blade is rounded and has a slender petiole 1½–2 inches long.

*Shoots*

The tender new leaves and shoots are amber in color, changing successively to tan, pale green, and then to dark green as they mature which colors are similar to those of the Duncan variety.

*Flower*

The slender flower panicles are 10–12 inches in length with slender, medium length laterals. The mid-stem, laterals and flowers are cream in color in early stages, darkening to light pink on aging. The fruit setting is good with very little shedding at any stage of development.

*Propagation*

This new variety is readily propagated vegetatively. The original seeding was inarched on a branch of an older tree. After fruiting, and on being found desirable, side or veneer grafts were employed in grafting young shoots on cutover trees for grove testing. Small plants have also been grafted to extend the variety. All procedures have been successful.

*Disease resistance*

The glossy upper surface of the leaves, and the smooth, glossy green of the developing fruit make this variety singularly free from Anthracnose fungus. With normal cultural practice the fruit develops and matures with a minimum of skin markings.

The growth of the young tree is generally upward, the branches opening outward with age and weight thereby forming an open top, with freedom of air and sunlight permitting fruit setting throughout the top of the tree.

By planned breeding the objective sought was a superior quality of mango, prolific in bearing, resistant to climatic conditions and disease, adequate in size and color for commercial purposes; by crossing the monoembryonic hybrid Kent with the better flavored monoembryonic hybrid Edward. Of the progeny obtained, this variety meets the requirements and characteristics of the objective sought.

Having thus described my invention, what is claimed is:

1. The variety of mango as described and shown herein.

No references cited.

ROBERT E. BAGWILL, Primary Examiner